United States Patent [19]
Cherney et al.

[11] Patent Number: 6,127,577
[45] Date of Patent: Oct. 3, 2000

[54] METHOD OF MAKING 3,5-DIFLUOROANILINE FROM 1,3,5-TRICHLOROBENZENE

[75] Inventors: Lee I. Cherney, Gahanna, Ohio; Francis J. Mettille, Wheaton, Ill.

[73] Assignee: BASF Corporation, Mount Olive, N.J.

[21] Appl. No.: 09/500,368

[22] Filed: Feb. 8, 2000

[51] Int. Cl.$^7$ .................................................. C07C 209/10
[52] U.S. Cl. ............................................................ 564/407
[58] Field of Search ............................................... 564/407

[56] References Cited

U.S. PATENT DOCUMENTS

| | | |
|---|---|---|
| 4,140,719 | 2/1979 | Tull et al. . |
| 4,145,364 | 3/1979 | Mulvey et al. . |
| 4,294,988 | 10/1981 | Tull et al. . |
| 4,343,951 | 8/1982 | Fifolt et al. . |
| 5,041,674 | 8/1991 | Pews et al. . |
| 5,091,580 | 2/1992 | Pews et al. . |
| 5,116,982 | 5/1992 | Fung et al. . |
| 5,157,169 | 10/1992 | Patton . |
| 5,294,742 | 3/1994 | Schach et al. . |
| 5,399,767 | 3/1995 | Nasu et al. . |
| 5,498,794 | 3/1996 | Schach et al. . |
| 5,510,533 | 4/1996 | Kobayashi et al. . |
| 5,679,879 | 10/1997 | Mercier et al. . |
| 5,856,577 | 1/1999 | Cordier et al. . |

OTHER PUBLICATIONS

Pews, R.G., "Aromatic Fluorine Chemistry, Part 4, Preparation of 2,6–Difluoroaniline", *J. Fluorine Chem.*, (1991), pp. 307–316, vol. 52, Month Available.

*Primary Examiner*—Samuel Barts
*Attorney, Agent, or Firm*—Alston & Bird LLP

[57] ABSTRACT

A method for manufacturing 3,5-difluoroaniline by fluorinating 1,3,5-trichlorobenzene and then aminating the intermediate fluorinated benzene with aqueous or anhydrous ammonia to achieve the product in yields of greater than 80%.

25 Claims, 5 Drawing Sheets

METHOD OF MAKING 3,5-DIFLUOROANILINE FROM 1,3,5-TRICHLOROBENZENE

FIELD OF THE INVENTION

The present invention relates to methods for manufacturing 3,5-difluoroaniline and compounds containing 3,5-difluoroaniline. More specifically, it relates to the manufacture of 3,5-difluoroaniline using 1,3,5-trichlorobenzene as a starting material, fluorinating the 1,3,5-trichlorobenzene to make a 1,3,5-trifluorobenzene intermediate compound, and then aminating the intermediate to make the desired 3,5-difluoroaniline.

BACKGROUND OF THE INVENTION

The compound, 3,5-difluoroaniline is a key intermediate in the synthesis of many broadleaf herbicides and other agricultural chemical and pharmaceutical products. Many synthetic routes to this compound have been investigated. However many such syntheses are difficult, or do not render a sufficient yield, or are simply too costly. For example, it is difficult to introduce two fluorine substituents in the 3 and 5 positions relative to amino- or nitro-functionality. For this reason, technically elaborate and expensive synthesis alternatives have been attempted. However, unfavorable yields and an abundance of interfering reaction byproducts make such syntheses impractical. In the realm of agricultural chemicals, cost studies have repeatedly indicated that only short synthetic pathways (3 steps or less) are economically feasible.

For example, syntheses displacing chloride by fluoride in 1,3,5-trichlorobenzene are known. However, the reaction time was slow with unacceptably low yields. R. G. Pews, in *J. Fluorine Chem.* Vol. 52, page 307 (1991), has suggested that faster reaction rates and higher yields could be obtained using an autoclave and different solvents. However when the reaction was run in N-methylpyrrolidone (NMP) using CsF and $KHF_2$ as catalysts, yields were not as high as those reported by Pews. Further, the use of NMP caused substantial halogen reduction.

U.S. Pat. No. 5,294,742 disclosed preparation methods for 3,5-difluoroaniline where 2,4,5-trichloronitrobenzene is used as a starting material and reacted with an alkali metal fluoride. However, the synthesis is complicated due to the multiple reaction steps, and the high quantities of by-product (20% 2,6-difluoroaniline) produced.

U.S. Pat. No. 5,399,767 discloses another complicated method comprising reacting a benzonitrile with a mineral acid, decarboxylizing to an intermediate, and reacting with hydrogen to make 3,5-difluoroaniline.

In view of the significant commercial use of 3,5-difluoroaniline, there has been substantial research directed to identifying commercially acceptable, safe, inexpensive and efficient methods for its manufacture in suitably high yields. However, there is no present method known for producing 3,5-difluoroaniline in high yields with few by-products to be separated, that is also safe and inexpensive.

SUMMARY OF THE INVENTION

One embodiment of the present invention relates to the discovery that 3,5-difluoroaniline can be synthesized at high yields and high purity by fluorinating 1,3,5-trichlorobenzene in the presence of a polar solvent to make an intermediate 1,3,5-trifluorobenzene, and then aminating the 1,3,5-trifluorobenzene in the presence of aqueous or anhydrous ammonia to obtain the desired 3,5-difluoroaniline.

In a further embodiment, the present invention relates to a method for the two step preparation of 3,5-difluoroaniline from 1,3,5-trichlorobenzene. First, an amount of 1,3,5-trichlorobenzene is reacted with a fluoride-containing compound to obtain 1,3,5-trifluorobenzene. Second, the 1,3,5-trifluorobenzene is reacted with aqueous ammonia and a metal oxide or metal hydroxide to obtain the product 3,5-difluoroaniline.

In a still further embodiment, the present invention contemplates a method for the two-step preparation of 3,5-difluoroaniline from 1,3,5-trichlorobenzene. First, an amount of 1,3,5-trichlorobenzene is reacted with an amount of a fluoride-containing compound to make 1,3,5-trifluorobenzene. Second, the 1,3,5-trifluorobenzene is reacted in a polar solvent with an amount of anhydrous ammonia to obtain 3,5-difluoroaniline.

DETAILED DESCRIPTION OF THE INVENTION

The present invention now will be described more fully with preferred embodiments of the invention shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The 3,5-difluoroaniline compound of formula (I) can be obtained by fluorinating the starting material, 1,3,5-trichlorobenzene of formula (II) via a Halex reaction to achieve the intermediate compound of formula (III) 1,3,5-trifluorobenzene.

(I)

-continued (II)

(III)

The first step of the preferred reaction scheme is shown below:

In this first step, referred to as the Halex reaction, the starting material 1,3,5-trichlorobenzene (II) is treated in a solvent with potassium fluoride. Small amounts of byproducts including 3,5-difluorochlorobenzene (IV) and large amounts of potassium chloride are produced, along with the desired intermediate compound, 1,3,5-trifluorobenzene (III).

Polar solvents are preferably used as the solvent for the Halex reaction used to fluorinate the 1,3,5-trichlorobenzene. Examples of preferred polar solvents include dimethylimidazolidinone (DMI), N-methyl-pyrrolidinone (NMP), dimethylpropylene urea (DMPU), tetramethyl urea (TMU) with DMI being particularly preferred.

The second step of the preferred reaction scheme is shown below:

In the second step 1,3,5-trifluorobenzene is reacted with ammonia (animation) to yield the desired product 3,5-difluoroaniline along with ammonium fluoride. The animation preferably takes place preferably in a polar organic solvent such as dimethylsulfoxide, N-methylpyrrolidone, propylene glycol, formamide, diethylene glycol, other polyglycols, dimethylformamide, dimethylacetamide, tetramethylene sulfone, dimethyl sulfone, diphenyl sulfone, polyglycol ethers, or N,N'-dimethylimidazolinone, with diethylene glycol being particularly preferred.

Aqueous or anhydrous ammonia may be used to aminate the 1,3,5-trifluorobenzene. Aqueous ammonia amination requires high pressures and temperatures. The ammonium fluoride generated is very corrosive under these conditions. Such corrosiveness can be controlled by adding bases as buffers, such as metal hydroxides and metal oxides including sodium hydroxide, calcium hydroxide, barium hydroxide, potassium hydroxide, magnesium hydroxide, magnesium oxide, calcium oxide, barium oxide, with magnesium oxide and magnesium hydroxide being particularly preferred. The magnesium oxide or magnesium hydroxide reacts to keep the fluoride as $MgF_2$, an insoluble solid. This allows the fluoride to be removed easily. In addition, as compared with the other metal oxides and hydroxides, fewer phenols and other by-products are formed.

The 1,3,5-trichlorobenzene (TCB) starting material is commercially available in acceptable purity grades. In the first step of the two-step reaction synthesis of the present invention, the TCB is preferably reacted in an autoclave, preferably equipped with a fractionating column, with dimethylimidazolidinone (DMI) and potassium fluoride at from about 275 to about 325° C., preferably from about 300 to about 315° C. to produce 1,3,5-trifluorobenzene with chlorodifluorobenzene as an impurity of <5% by-product weight.

The yield of the intermediate, 1,3,5-trifluorobenzene (TFB) may be tailored by altering variables including reaction temperature and water content. For example, it was determined that when the preferred solvent DMI was distilled to approximately 90% of its volume, the reaction rate increased and the yield was increased to about 83%. Therefore, it is desirable to dehydrate the reagents used, including DMI and KF. This can be done by distilling about 10% of the solvent, or by adding a solvent such as xylene to scavenge water such as by azeotropic distillation.

The preferred Halex reaction used to prepare the intermediate TFB can be run in the presence of an excess of KF. However, it was determined that molar equivalents of KF in the range of from about 3.2 to about 6.0 did not materially affect the reaction rate of formation of TFB.

The intermediate TFB yield preferably also can be optimized by removing TFB from the reaction vessel as it is formed to reduce the formation of byproducts. The preferred pressure distillation can be improved if a fractionating column is heated such as by applying a heating tape to the column or otherwise insulating the column.

While the process of the present invention is not dependent upon specific reagent stoichiometry and instrumentation, the ratio of approximately 1.5 moles of 1,3,5-trichlorobenzene per liter of DMI solvent is particularly preferred. Potassium fluoride is preferably loaded into the reaction vessel at a constant of approximately 330 g/kg DMI. If it is so desired, various reactants may be recovered and reused. For example, relatively expensive solvents such as DMI can be recovered by filtering the KCl/KF salt precipitate during the Halex reaction. The precipitate is then washed with an inexpensive, low-boiling, solvent, e.g. MTBE (or methylene chloride) to recover the DMI entrained in the salts. Distillation of the recycled solvent is advisable for optimum yields in the Halex reaction. Alternative solvents to DMI for the Halex reaction of the present invention include tetramethyl urea (TMU), dimethylsulfone ($DMSO_2$) and dimethylpropylene urea (DMPU). NMP has been used successfully but requires the addition of 1,3-dinitrobenzene or similar radical scavengers to reduce by-products resulting from hydro-dehalogenation.

In the second step of the synthesis of the present invention, the TFB is aminated by adding ammonia with or without a second solvent. Either aqueous ammonia or anhydrous ammonia may be used. In the second step, according to the process of the present invention, 1,3,5-trifluorobenzene (TFB) is reacted with ammonia in the presence of water or polar solvent such as NMP, propylene glycol, glycol ethers, or most preferably diethylene glycol (DEG). However higher yields of the product 3,5-difluoroaniline were obtained when the anhydrous ammonia was reacted with the TFB in certain polar solvents.

When water is used, corrosion of the reactors can be significant and buffering with metal oxides or hydroxides, such as sodium hydroxide, calcium oxide, magnesium hydroxide and preferably magnesium oxide, is useful in preventing such corrosion. Using buffers that form insoluble fluorides such as magnesium fluoride ($MgF_2$) allows the easy isolation and removal of fluoride ions from the reaction mixture by filtration. Using magnesium oxide or magnesium hydroxide is preferred since both excess buffer and $MgF_2$ can be removed together by filtration. Additionally, their low solubility prevents generating hydroxyl ions which react with TFB to form phenolic by-products. Temperatures of from about 180 to about 250° C. are preferred, with temperatures of from about 210 to about 235° C. being most preferred. The performance of the magnesium oxide and magnesium hydroxide was unexpected since their performances were much better than their calcium counterparts.

The preferred synthesis condition of the present invention as set forth in the following examples produce 3,5-difluoroaniline with a minimum of accompanying byproducts. Specifically, in the amination step (step 2), 3,5-difluorophenol and bis-(3,5-difluorophenyl) ether are produced, especially when a base is present. Other tetrahaloethers are produced in very small amounts. Diaminofluorobenzene may also be produced in an amount of from about 3% to about 5%. It was found that conducting the step 2 synthesis at "lower" temperatures, preferably at from about 180 to about 250° C., and more preferably 235° C., generally reduced the formation of byproducts.

Figure 1:
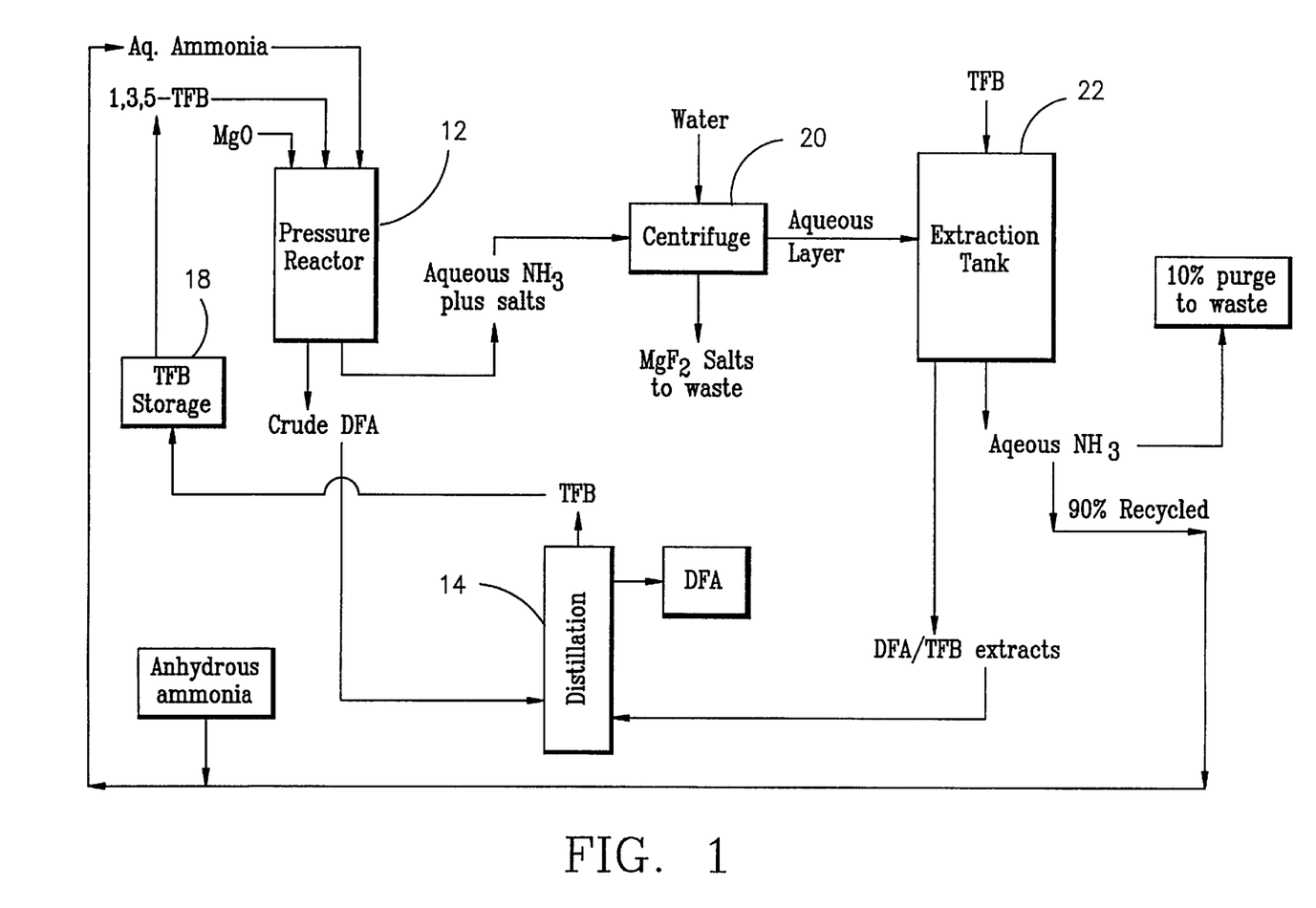
FIG. 1 is a block flow diagram of the reaction of 1,3,5-trifluorobenzene with aqueous ammonia showing the direct recycling of ammonia.

FIG. 1 shows a block flow diagram of the preferred equipment set up for the reaction of TFB with ammonia whereby the ammonia is recycled. Aqueous ammonia, TFB and MgO are introduced to the pressure reactor 12. The crude 3,5-difluoroaniline (DFA) is removed from the reactor and further distilled 14 to produce TFB and final DFA product 16. The TFB is directed to TFB storage tank 18 and supplied as starting material to replenish the pressure reactor 12. Aqueous ammonia and salts are removed from the pressure reactor 12 and directed to centrifuge 20 where the salts are washed with water. Magnesium fluoride salts are removed from the centrifuge as the aqueous layer is sent to extraction tank 22. Additional TFB is supplied to the tank 22 to extract any DFA dissolved in the aqueous material. DFA/TFB extracts are removed from tank 22 and directed to distillation apparatus 14. Aqueous ammonia leaves the extraction tank 22 where about 10% is purged (to prevent waste buildup from the MgO, HF and water) and the remaining 90% is re-fortified with anhydrous ammonia and recycled to the reactor. To control corrosion, additional buffers such as magnesium hydroxide, barium hydroxide, and calcium oxide may be used so long as phenol formation is not increased by their use.

The product, 3,5-difluoroaniline (DFA) is formed in the oil phase of the reactor contents, with up to about 10% also held in the aqueous layer. The oil layer, containing, containing DFA, water (5–10%) and ammonia was separated from the water/ammonia/magnesium salt phase, and then the aqueous layer is extracted with TCB. Subsequent distillation realized yields of DFA using the process of the present invention in excess of 85% by weight.

Figure 2:
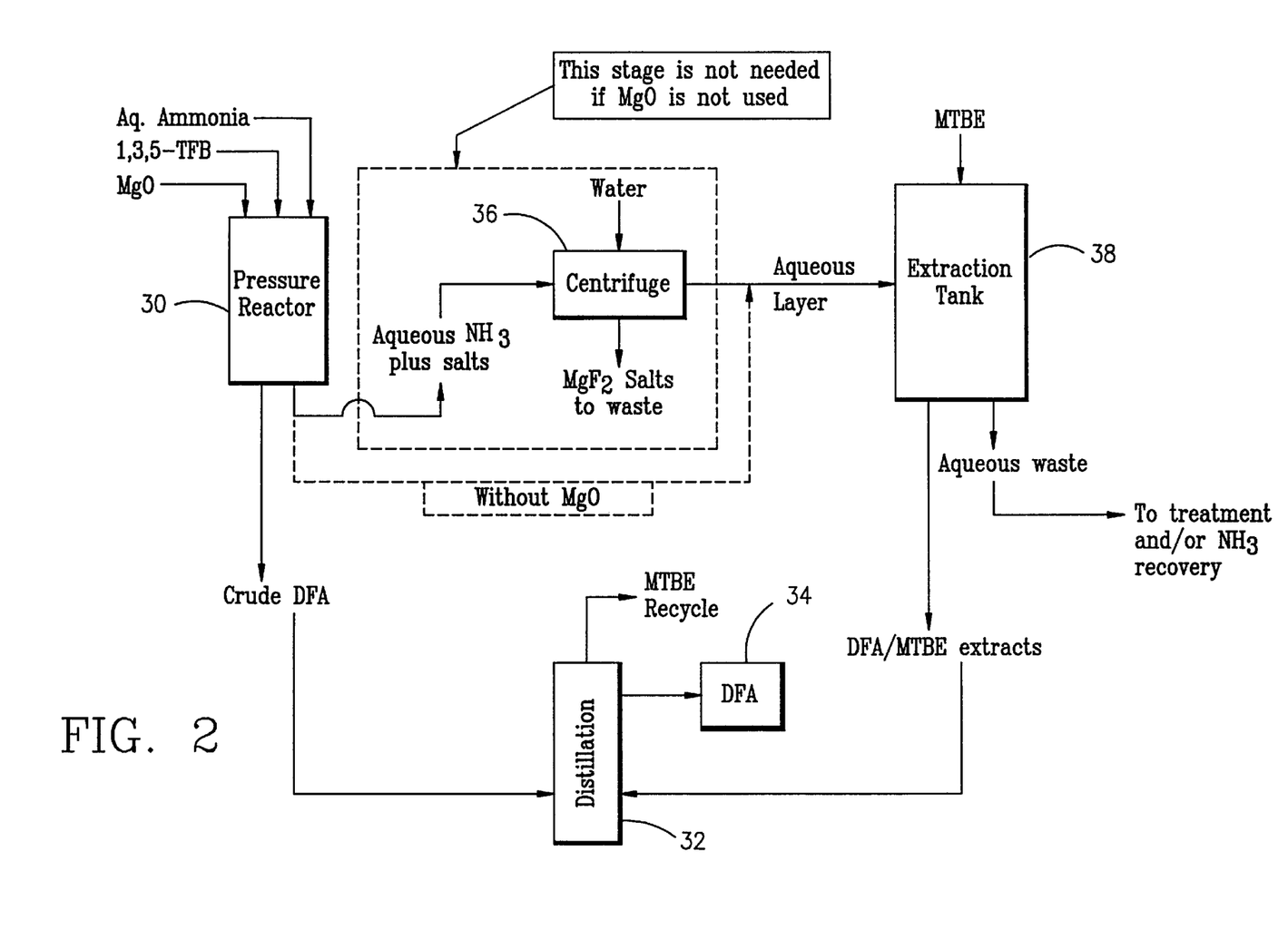
FIG. 2 is a block flow diagram of the reaction of 1,3,5-trifluorobenzene where ammonia is reprocessed or discarded.

FIG. 2 shows a reaction of TFB with ammonia in block diagram form where the ammonia is discarded. Aqueous ammonia, TFB and MgO are introduced into a pressure reactor 30. Crude DFA produced is removed from reactor 30 and distilled in distillation apparatus 32 to fine DFA product 34. The aqueous layer from the reaction is transferred to tank 38 where it is extracted with MTBE to recover additional DFA. This is also sent to distillation apparatus 32 where the solvent MTBE is distilled out and collected for recycling and the DFA is purified. If MgO is added as a catalyst to the reactor, aqueous ammonia and salts are directed from reactor 30 to centrifuge 36. Water is introduced and $MgF_2$ salts are removed as waste from the centrifuge 36. The aqueous layer is then directed to the extractions tank 38 into which MTBE is directed. When MgO is not used in the reaction, the centrifuge step is obviated. Aqueous waste is voided from the extraction tank 38 and further treated or discarded.

Alternatively, the reaction of TFB with anhydrous ammonia can be run in the presence of a polar solvent such as NMP, sulfolane, glycol ethers, propylene glycol, and most preferably diethylene glycol. Using polar solvents results in slightly higher product yields than the aqueous system. The reaction pressure required is also reduced significantly. The potential for corrosion is also reduced due to the reaction being able to run at lower temperatures. The preferred reaction temperatures are comparable for both aqueous and anhydrous reaction systems.

The presence of a buffer used with aqueous ammonia will reduce the corrosive effect of the heated ammonia. Therefore the process of the present invention contemplates the use of reaction vessels such as Hastelloy that is able to withstand harsh reaction conditions when buffers are not used. However, when buffers, preferably the metal oxides and hydroxides such as magnesium oxide and magnesium hydroxide, are present in the aqueous ammonia, the contents are less corrosive and reaction vessels made from carbon steel and stainless steel may be used.

Suitable solvents into which the TFB and ammonia are placed include N-methylpyrrolidone (NMP), DMI, sulfolane, dimethyl sulfoxide, propylene glycol, formamide, and diethylene glycol. When an anhydrous ammonia is used in NMP, reaction yields increased in small scale (2 gallon) syntheses to >95%. When anhydrous ammonia is used, additives are desired, and may include ethanol, isopropanol, propylene glycol, etc.

Figure 3:
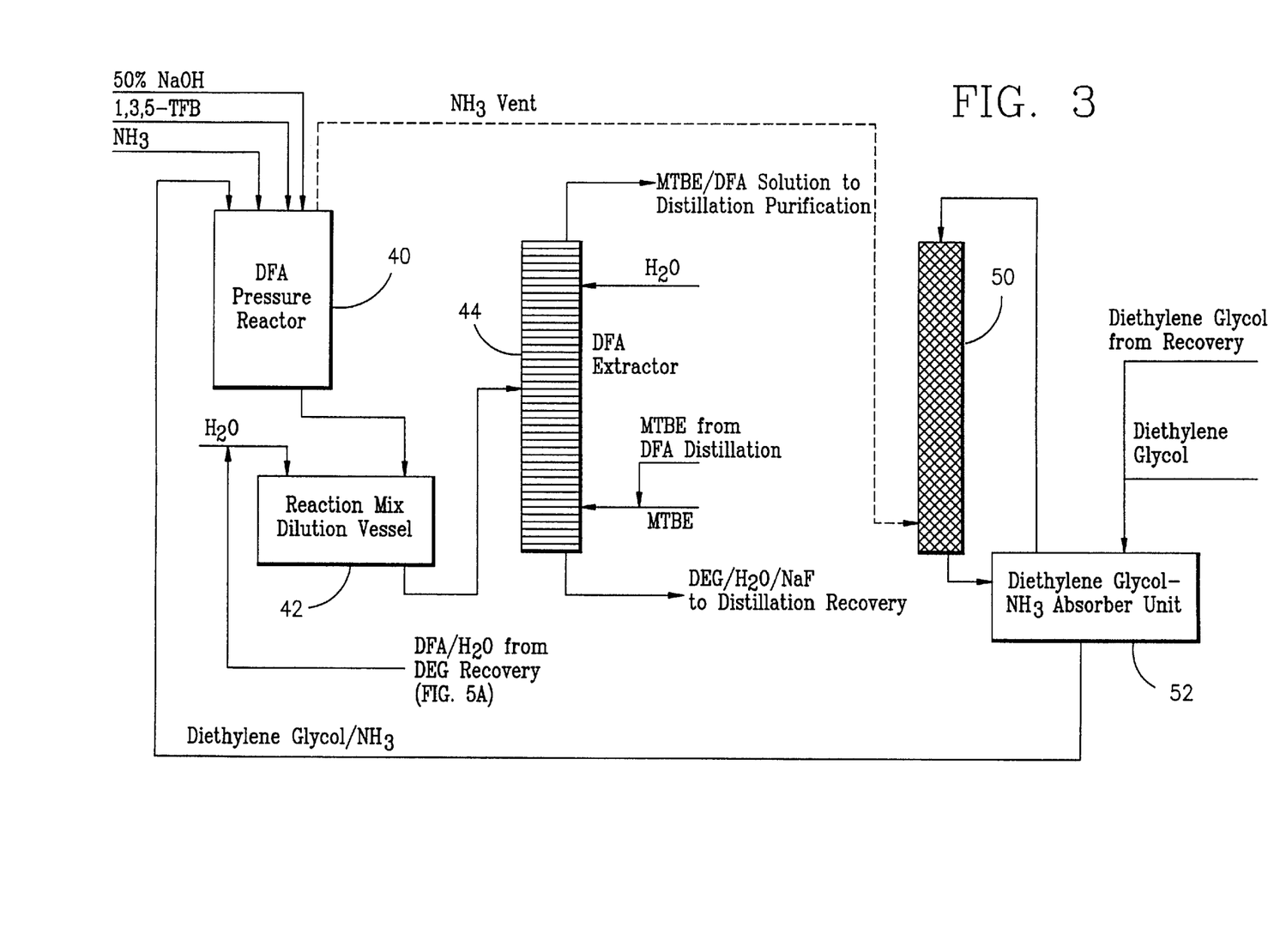
FIG. 3 is a block flow diagram of the 3,5-difluoroaniline synthesis showing the use of anhydrous ammonia in a solvent coupled with an extractive isolation.

FIG. 3 shows an alternate embodiment of the process for the second step (TFB animation) whereby diethylene glycol (DEG) is recycled and added to the reaction chamber 40 along with ammonia, 50% sodium hydroxide solution (NaOH) and TFB. The mixture is reacted and directed to a dilution vessel 42 into which water is added preferably with a DFA/H$_2$O for DEG recovery step. The treated hydrated mixture proceeds to a DFA extractor 44 where MTBE and water are supplied. An MTBE/DFA solution is directed to distillation purification shown in FIG. 5A. A DEG/H$_2$O/NaF mixture is directed to distillation recovery S5. Excess ammonia is directed from the starting reaction chamber via an NH$_3$ vent 50 to a packed column into where it is recovered by absorption in DEG. Parts 50 and 52 constitute the DEG/NH$_3$ absorber unit.

Figure 4:
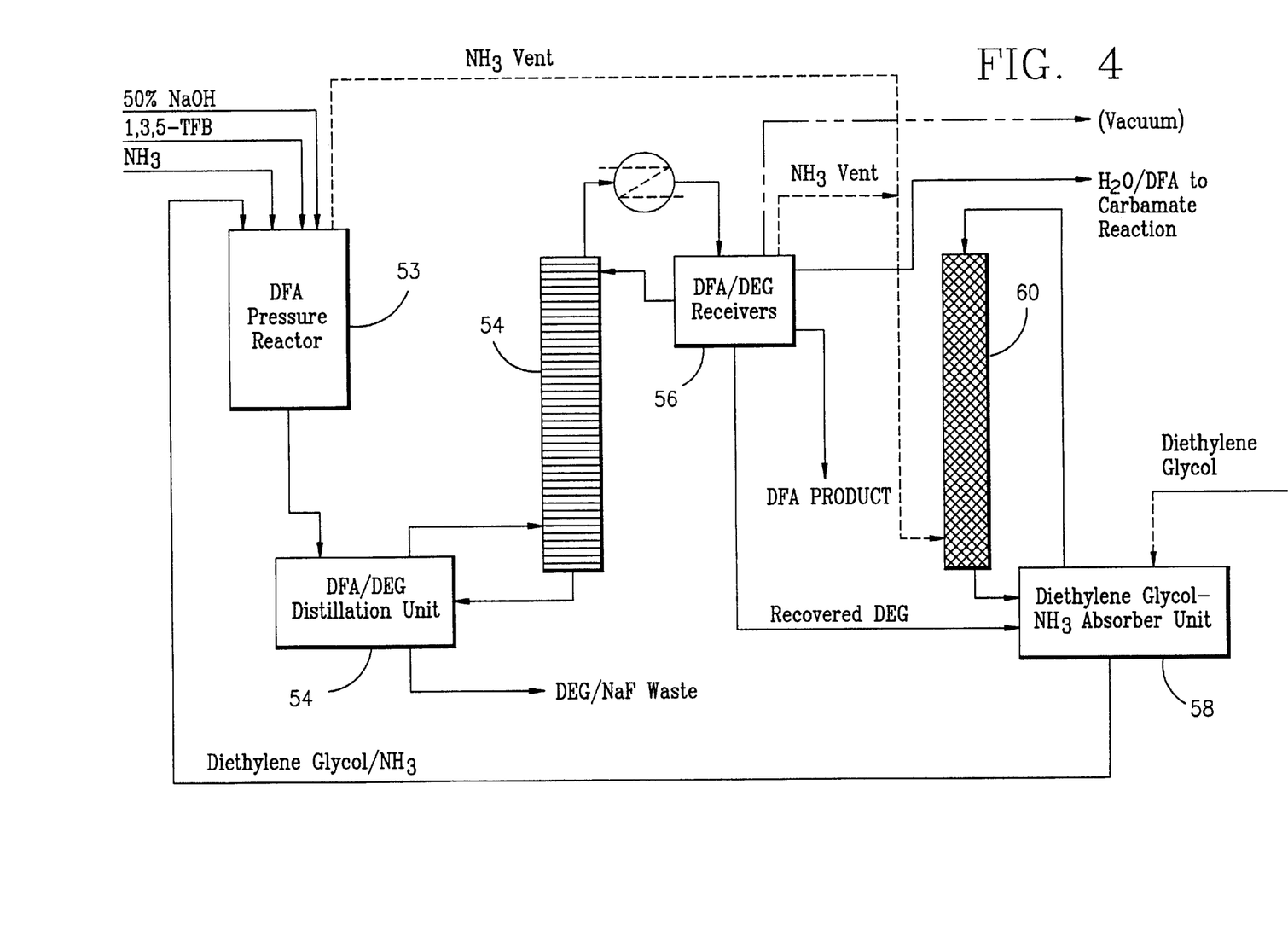
FIG. 4 is a block flow diagram of the 3,5-difluoroaniline synthesis showing the use of anhydrous ammonia in a solvent followed by distillation isolation.

FIG. 4 shows a block diagram for the preferred processing of TFB to 3,5-DFA by an anhydrous ammonia, distillation isolation process. Amounts of 50% NaOH, TFB and NH$_3$ are supplied to the DFA pressure reactor 53. The product proceeds to the DFA/DEG distillation unit 54 with DEG/NaF waste being removed from the system. The crude DFA proceeds through column 54 and into the DFA receiver 56. DFA product is collected from the receiver, with recovered DEG from the DEG receiver and is directed to the DEG-NH$_3$ absorber unit 58 being vented and directed to column 60. H$_2$O/DFA is directed out of receiver 56 to a carbonate reaction.

Figures 5A, 5B:
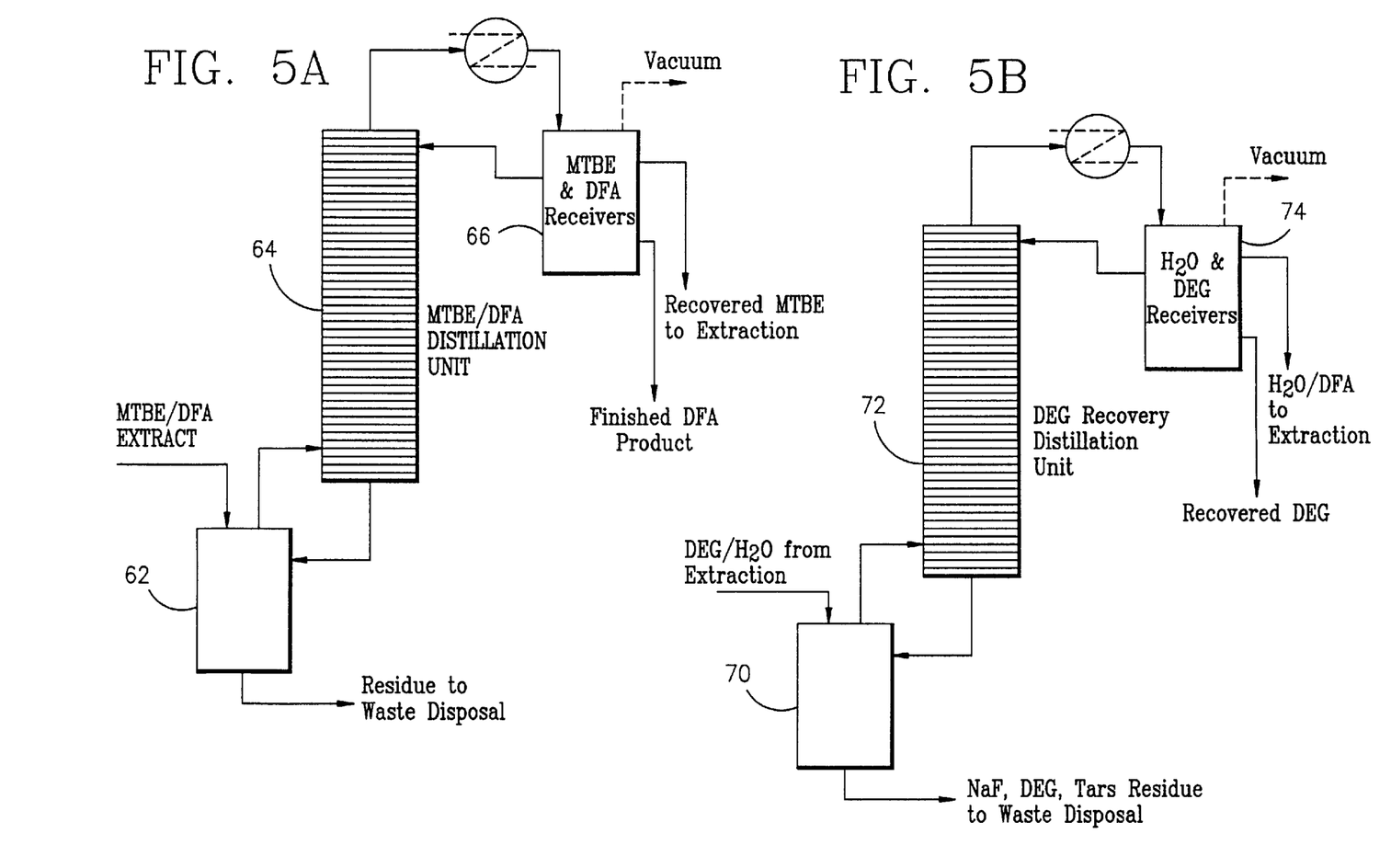
FIGS. 5a and 5b are block flow diagrams of the 3,5-difluoroaniline synthesis showing respectively the extractive isolation and 3,5-difluoroaniline and solvent recovery.

FIGS. 5A and 5B are schematic characterizations of a preferred 3,5-DFA extractive isolation for recovering DFA. In FIG. 5A, MTBE/DFA extract is collected, for example, from the process of FIG. 3 and collected in reservoir 62 before being directed to MTBE/DFA distillation unit 64. The MTBE/DFA is directed to the MTBE/DFA receiver 66 under vacuum where "finished" DFA product and MTBE are then separately recovered.

When DEG is used as the solvent, as shown in FIG. 5B, DEG/H$_2$O from an extraction step is directed to reservoir 70 from which NaF, some DEG mixed with tars, and residue are removed as waste. DEG is further processed in the DEG recovery unit 72 before being diverted to the H$_2$O and DEG receiver 74. H$_2$O/DFA is then directed to further extraction and the recovered DEG is ready for removal or recycling.

The present invention is further explained with reference to the following examples, but the invention should not be construed as being limited thereto.

EXAMPLE 1
Preparation of 1,3,5-trifluorobenzene

A two gallon (7.8 liter) stirred stainless steel pressure reactor (Parr Instrument Co., Moline, Ill.) was equipped with a 1"×10" stainless steel distillation column packed with ProPak extruded metal packing. The top of the column was fitted with a reflux condenser and needle valves for venting gases and removing product. A thermocouple was fitted just above the column packing. The column was wrapped with heating tape and insulation to minimize heat loss. The reactor was charged with 33.4 moles of dry N,N'-dimethylimidazolidinone (DMI) (3800 g), 6.15 moles of 1,3,5-trichlorobenzene (TCB) (1118 g) and 22.2 moles of potassium fluoride (KF) (1286 g). The reactor was then sealed. Nitrogen was twice charged (200 psig), then vented to remove air. The reactor was then stirred vigorously (760 r.p.m.) and heated to from about 310° C. to about 315° C. After reaching 310° C., nitrogen was vented from the reactor through the valve at the top of the condenser. After from about 2 to about 2.5 hours heating, the TFB produced was distilled off slowly through the take-off valve at the top of the condenser at a rate of about 100 ml/hr. The TFB was removed over a period of from about 6 to about 7 hours. The reactor was then cooled and the salts were filtered off from the DMI. The salts were washed with methylene chloride to recover all the DMI. Alternately, other solvents, such as methyl t-butyl ether (MTBE), could also be used. The filtrate and solvent washes were combined and distilled for recovery of both the wash solvent and DMI. Distillation of MTBE was done at atmospheric pressure while DMI was recovered by reduced pressure distillation of about 118° C.@28 mm Hg. For high purity, the TFB must be re-distilled.

EXAMPLE 2
Preparation of 3,5-difluoroaniline

A 600 ml Hastelloy pressure reactor (Parr Instrument Co., Moline, Ill.) equipped with the standard stirrer, thermowell, and valves was used. The reactor was charged with 0.833 moles of 1,3,5-trifluorobenzene (110 g), 4.6 moles of 29% ammonia in water (270 g), and 0.44 moles of magnesium oxide (17.8 g). The reactor was purged with argon, and heated to 225° C. until the maximum pressure (about 1400 psig) was reached. As the reaction proceeded, the pressure dropped at a rate of about 20 lbs./hour for about 6 hours. The reactor was then cooled and the contents allowed to settle. The oils were drained from the reactor bottom until salts/water are observed. The salts float on the oils and settle slowly in the aqueous ammonia. The aqueous salts were extracted 2 or 3 times with MTBE. The MTBE was combined with the oils and charged to a distillation column packed with stainless steel packing (ProPak). The salts were centrifuged, washed with water, and discarded. The product was isolated by distilling MTBE at atm. Pressure, then distilling DFA at 20 to 50 mm.

EXAMPLE 3
1,3,5-tifluorobenzene in DEG

An amount of 1,3,5-trifluorobenzene (TFB) was initially reacted with anhydrous NH$_3$ in diethylene glycol (DEG) at 200° C. The reaction was unacceptably slow and gave approximate 17% conversion to product in three hours. The reaction was subsequently carried out at 230° C. Maximum pressure was 960 psig. After 10 hours, conversion of TFB to 3,5-difluoroaniline (DFA) was 95%. Overall accountability by gas chromatograph assay was 97%.

EXAMPLE 4
3,5-Difluoroaniline Recovery by Distillation

A 300 ml. 316SS Parr autoclave was charged with 50.9 g. (0.385 eq.) of 1,3,5-trifluorobenzene (TFB) and 150 ml. (167 g) of diethylene glycol (DEG). The sealed autoclave was then charged with 26.6 g of anhydrous NH$_3$ from a cylinder. The ratio was 4 equivalents NH3 per equivalent of (TFB). The autoclave was then heated to 230 C and held for 10.5 hours while agitating. The initial maximum pressure was 960 psig. Analysis after 7 hours indicated 84% conversion of TFB to product, 3,5-difluoroaniline (DFA), and the pressure had decreased to 440 psig. After 10.5 hours the pressure had decreased to 415 psig. Assay of the reactor indicated a 94% conversion of the TFB to DFA. Assay also indicated the presence of 43.6 g of DFA (0.338 eq.); 3.2 g of TFB (0.024 eq.); and 0.2 g (0.002 eq) of diaminofluorobenzene by-product. These results indicated 95% accountability and 94% selectivity of TBA to DFA. The autoclave was then cooled to 100 C and the excess NH$_3$ vented to a DEG absorber containing 150 ml of DEG. The DEG/NH$_3$ solution was recycled as solvent in a subsequent reaction.

The autoclave was then cooled to ambient temperature and the reaction slurry (including the solid NH$_4$F) was transferred to a vacuum distillation system. The distillation system consisted of a 2'×1" column packed with ¼" ceramic saddles. The pH of the slurry was 10.0. An amount of 30.1 grams (0.367 eq.) of 50% NaOH was added to neutralize the $NH_4F$ and generate free $NH_3$. The pH was 12.7 and a slurry of very fine crystalline NaF was formed. The slurry was then heated slowly to 100° C. and an additional 4.6 g. of $NH_3$ collected in the ammonia absorber. A total of 16.0 g of $NH_3$ was recovered (81% recovery). The remaining $NH_3$ (still dissolved in the reaction slurry) was lost in the subsequent vacuum distillation. The small amount of unreacted TFB in the reaction slurry is also collected in the absorber during the $NH_3$ venting and would be recycled to a subsequent reaction.

The resultant slurry was then vacuum distilled at 50 mm Hg pressure and a reflux ratio of 3: 1. An initial two-phase fraction of $H_2O$ and pure DFA (>99% excluding $H_2O$) was obtained at an O.H. temperature of 37.5 to 105.0° C. and pot temperature of 60.8 to 162.8° C. A total of 19.8 g of aqueous phase containing 0.4 g DFA and 35.8 g of DFA phase containing 2.2% $H_2O$ were collected. A second fraction temperature of DEG was taken at an O.H. temperature of 105.0 to 161.0° C. and pot temperature of 162.8 C to 166.7° C. A total of 13.8 g was collected which contained 8.7 g of DFA. A total of 44.1 g of DFA was accounted for through the distillation. No loss of DFA was encountered. The recovery represents a selectivity of TBA to DFA of about 89%. A total of 55.7 g of semisolid pot residue was obtained. The recovery of DEG for recycle was 75%. The bulk of the remaining DEG was left in the pot residue to fluidize the NaF and tars.

EXAMPLE 5
3,5-Difluoroaniline Recovery via Extraction with MTBE

A reaction similar to that of Example 4 was set up. The TFB charge was 50.0 g (0.379 eq) the $NH_3$ charge was 25.8 g (1.52 eq.) and the DEG charge was 150 ml (167.0 g). After 10.5 hours at 230° C., assay indicated 94% conversion of TFB. Assay also indicated the presence of 42.5 g (0.329 eq.) of DFA, 3.2 g (0.025 eq.) of TFB, and 0.4 g (0.003 eq) of 3,5-diaminoflourobenzene. This shows a 94% accountability of TFB and a 93% selectivity as described above. A total of 15.7 g of $NH_3$ was recovered in the DEG absorber for recycle (80%). The residual free $NH_3$ remains dissolved in the reaction slurry.

The reaction slurry was then diluted with an equal weight of $H_2O$. This serves to dissolve the NaF present and provide a solution which can then be extracted with MTBE. The DEG/DFA reaction solution alone is soluble in MTBE and does not provide a second phase for DFA extraction. The aqueous DEG solution was then extracted twice with MTBE. The first time with approximately 0.4 lbs. Of MTBE per lb. Of solution and the second time with approximately 0.1 lbs. MTBE per lb. of solution.

The desired goal in this extraction process is to use the DFA in the solvent for subsequent processing. Assay indicated that 42.6 g of DFA had been recovered in the MTBE (24.9% solution) and only 0.7 g. remained in the DEG/$H_2O$ phase. The recovery represents a 94% selectivity of TFB to DFA. Recovery of DFA from the reaction solution into the MTBE was 98.4%. Extractive recovery of the DFA was very efficient. The MTBE extract also contained approximately 1.0% DEG and would therefore not be suitable for direct use. A single water wash with about 0.3 lbs. Of $H_2O$ per lb. Of MTBE extract removed essentially all DEG from the MTBE/DFA solution. After extraction the DFA in the MTBE was 96–97% pure (gc area %). The DEG was isolated by vacuum distillation of the DEG/$H_2O$ solution (400.5 g) recovered from the extraction. The water was first removed at a pressure of 100 mm Hg and reflux ratio of 1.5:1. The O.H. temperature was 57.4 to 58.5° C. and pot temperature of 64 to 85° C. The DEG was recovered at 50 mm Hg. The O.H. temperature was 160.8 to 161.2° C. and the pot temperature was 168 to 171° C. A total of 132.6 g of DEG (79%) was left in the distillation bottoms to fluidize the NaF and residual reaction tars.

What is claimed is:

1. A process for providing 3,5-difluoroaniline from 1,3,5-trichlorobenzene comprising the steps of:

a) providing an amount of 1,3,5-trichlorobenzene to a reactor;

b) fluorinating the 1,3,5-trichlorobenzene to make a 1,3,5-trifluorobezene intermediate compound; and c) aminating the 1,3,5-trifluorobenzene to make 3,5-difluoroaniline.

2. The process according to claim 1, wherein the step of fluorinating the 1,3,5-trichlorobenzene comprises providing a fluoride of lithium, sodium, potassium, rubidium, cesium, or a mixture thereof.

3. The process according to claim 1, wherein the step of fluorinating the 1,3,5-trichlorobenzene comprises providing an amount of potassium fluoride.

4. The process according to claim 1, wherein the step of fluorinating the 1,3,5-trichlorobenzene comprises maintaining a temperature of from about 150° C. to about 400° C.

5. The process according to claim 1, wherein the step of fluorinating the 1,3,5-trichlorobenzene comprises maintaining a temperature of from about 250° C. to about 350° C.

6. The process according to claim 1, wherein the step of fluorinating the 1,3,5-trichlorobenzene comprises maintaining a temperature of from about 290° C. to about 320° C.

7. The process according to claim 1, and further comprising distilling under pressure the 1,3,5-triflourobenzene from the reactor as it is formed.

8. The process according to claim 1, wherein the step of fluorinating the 1,3,5-trichlorobenzene comprises providing a polar solvent.

9. The process according to claim 8, further comprising dehydrating the polar solvent prior to providing the 1,3,5,trichlorobenzene.

10. The process according to claim 1, wherein the step of flourinating the 1,3,5-tricholorbenzene comprises providing potassium flouride and the potassium flouride is dehydrated.

11. The process according to claim 8 further comprising providing an amount of 1,3-dinitrobenzene in an amount of up to about 10 mole %.

12. The process according to claim 8, wherein the polar solvent is selected from the group consisting of dimethyl sulfone, hexamethyl phosphoric triamide, sulfolane, N,N-dimethylpropylene urea, tetramethylurea, and N,N'-dimethylimidazolidinone.

13. The process according to claim 1, wherein the step of aminating the 1,3,5-trifluorobenzene comprises providing an amount of ammonia.

14. The process according to claim 13, wherein the ammonia is aqueous ammonia.

15. The process according to claim 14, wherein the ammonia concentration is from about 20% to about 50%.

16. The process according to claim 1, wherein the step of aminating the 1,3,5-trifluorobenzene comprises providing an amount of buffer into the aqueous ammonia.

17. The process according to claim 16, wherein the buffer is a metal oxide.

18. The process according to claim 16, wherein the buffer is a metal hydroxide.

19. The process according to claim 17, wherein the metal oxide is selected from the group consisting of magnesium oxide, calcium oxide, and barium oxide.

20. The process according to claim 19, wherein the metal hydroxide is selected from the group consisting of magnesium hydroxide, calcium hydroxide, sodium hydroxide, potassium hydroxide and barium hydroxide.

21. The process according to claim 17, wherein the metal oxide is magnesium oxide.

22. The process according to claim 18, wherein the metal hydroxide is magnesium hydroxide.

23. The process according to claim 1, wherein the step of aminating the 1,3,5-trifluorobenzene to make 3,5-difluoroaniline comprises providing an amount of anhydrous ammonia.

24. The process according to claim 23, wherein the step of aminating the 1,3,5-trifluorobezene comprises providing a polar solvent having the general schematic representation: RO—$(CH_2—CH_2O)_n$—OR wherein;

R=H, alkyl, aryl; and

N=1 to 200.

25. The process according to claim 24, wherein the polar solvent is selected from the group consisting of dimethylsulfoxide, N-methylpyrrolidone, propylene glycol, formamide, diethylene glycol, dimethyl formamide, dimethylacetamide, tetramethyl sulfone, dimethyl sulfone, diphenyl sulfone, tetramethyl urea, N,N'-dimethylpropylene urea, hexamethyl phosphoric triamide, and N,N'-dimethylimidazolidinone.

* * * * *